(12) United States Patent
Cohen

(10) Patent No.: US 9,579,830 B2
(45) Date of Patent: Feb. 28, 2017

(54) METHOD AND SYSTEM FOR MANUFACTURING INTEGRATED FLUIDIC CHIPS

(75) Inventor: David S. Cohen, San Bruno, CA (US)

(73) Assignee: Fluidigm Corporation, South San Francisco, CA (US)

( * ) Notice: Subject to any disclaimer, the term of this patent is extended or adjusted under 35 U.S.C. 154(b) by 1227 days.

(21) Appl. No.: 13/813,625

(22) PCT Filed: Jul. 23, 2009

(86) PCT No.: PCT/US2009/051568
§ 371 (c)(1),
(2), (4) Date: Sep. 17, 2014

(87) PCT Pub. No.: WO2010/011852
PCT Pub. Date: Jan. 28, 2010

(65) Prior Publication Data
US 2015/0273735 A1    Oct. 1, 2015

Related U.S. Application Data

(60) Provisional application No. 61/083,877, filed on Jul. 25, 2008.

(51) Int. Cl.
*B01L 3/00* (2006.01)
*B32B 37/18* (2006.01)
(Continued)

(52) U.S. Cl.
CPC .............. *B29C 41/02* (2013.01); *B01L 3/502* (2013.01); *B01L 3/502707* (2013.01);
(Continued)

(58) Field of Classification Search
CPC ....... B01L 2300/0861; B01L 2300/123; B01L 2400/0481; B01L 2400/0655; B01L 3/502;
(Continued)

(56) References Cited

U.S. PATENT DOCUMENTS 6,251,343 B1 *   6/2001   Dubrow ........... G01N 27/44791
                                                              422/503
6,540,895 B1     4/2003   Spence et al.
(Continued)

FOREIGN PATENT DOCUMENTS

CN       1369039 A        9/2002
JP     2007-516602 T2     6/2007
(Continued)

OTHER PUBLICATIONS

Fiorini et al., "Disposable Microfluidic Devices: Fabrication, Function, and Application", BioTechniques 38:429-446, Mar. 2005, p. 430 paragraph 4.

(Continued)

*Primary Examiner* — Jennifer Wecker
(74) *Attorney, Agent, or Firm* — Kilpatrick Townsend & Stockton LLP

(57) ABSTRACT

An integrated fluidic chip includes a substrate defined by a lateral surface area greater than 28 square inches. The integrated fluidic chip also includes a first elastomeric layer having a mold surface and a top surface. The mold surface of the first elastomeric layer is joined to a portion of the substrate. The first elastomeric layer includes a plurality of first channels extending normally from the substrate to a first dimension inside the first elastomeric layer. The integrated fluidic chip further includes a second elastomeric layer having a mold surface and a top surface. The mold surface of the second elastomeric layer is joined to at least a portion of the top surface of the first elastomeric layer.

39 Claims, 10 Drawing Sheets

(51) Int. Cl.
| | |
|---|---|
| *B32B 38/00* | (2006.01) |
| *B29C 41/02* | (2006.01) |
| *G01N 30/60* | (2006.01) |
| *B29K 83/00* | (2006.01) |
| *B29L 9/00* | (2006.01) |
| *B29L 31/00* | (2006.01) |

(52) U.S. Cl.
CPC ........ *B32B 37/182* (2013.01); *B32B 38/0008* (2013.01); *B01L 2300/0861* (2013.01); *B01L 2300/123* (2013.01); *B01L 2400/0481* (2013.01); *B01L 2400/0655* (2013.01); *B29K 2083/00* (2013.01); *B29L 2009/00* (2013.01); *B29L 2031/755* (2013.01); *B32B 2309/105* (2013.01); *B32B 2383/00* (2013.01); *G01N 30/6095* (2013.01)

(58) Field of Classification Search
CPC ............... B01L 3/502707; B29C 41/02; B29K 2083/00; B29L 2009/00; B29L 2031/755; B32B 2309/105; B32B 2383/00
See application file for complete search history.

(56) References Cited

U.S. PATENT DOCUMENTS

| | | | |
|---|---|---|---|
| 6,860,956 B2 * | 3/2005 | Bao | B82Y 10/00 156/232 |
| 6,885,982 B2 | 4/2005 | Harris et al. | |
| 6,951,632 B2 | 10/2005 | Unger et al. | |
| 7,042,649 B2 | 5/2006 | Quake et al. | |
| 7,059,348 B2 | 6/2006 | Nat | |
| 7,062,418 B2 | 6/2006 | Lee et al. | |
| 7,097,809 B2 | 8/2006 | Dam et al. | |
| 7,161,736 B2 | 1/2007 | Legrand et al. | |
| 7,192,629 B2 | 3/2007 | Lammertink et al. | |
| 7,217,367 B2 | 5/2007 | Huang et al. | |
| 7,232,109 B2 | 6/2007 | Driggs et al. | |
| 7,248,413 B2 | 7/2007 | Quake et al. | |
| 7,262,923 B2 | 8/2007 | Quake et al. | |
| 7,279,146 B2 | 10/2007 | Nassef | |
| 7,291,512 B2 | 11/2007 | Unger | |
| 7,294,503 B2 | 11/2007 | Quake et al. | |
| 7,368,163 B2 | 5/2008 | Huang et al. | |
| 7,442,556 B2 | 10/2008 | Manger et al. | |
| 7,476,363 B2 | 1/2009 | Unger et al. | |
| 7,526,741 B2 | 4/2009 | Lee et al. | |
| 7,604,965 B2 | 10/2009 | McBride et al. | |
| 7,666,361 B2 | 2/2010 | McBride et al. | |
| 7,678,547 B2 | 3/2010 | Eyal et al. | |
| 7,691,333 B2 | 4/2010 | McBride et al. | |
| 7,749,737 B2 | 7/2010 | McBride et al. | |
| 7,792,345 B2 | 9/2010 | Taylor et al. | |
| 7,815,868 B1 | 10/2010 | Jones et al. | |
| 7,820,427 B2 | 10/2010 | Unger et al. | |
| 7,833,708 B2 | 11/2010 | Enzelberger et al. | |
| 7,837,946 B2 | 11/2010 | McBride et al. | |
| 2004/0180377 A1 | 9/2004 | Manger et al. | |
| 2005/0000900 A1 * | 1/2005 | Huang | G01N 30/6095 210/656 |
| 2005/0053952 A1 * | 3/2005 | Hong | B01L 3/50273 435/6.14 |
| 2005/0079104 A1 * | 4/2005 | Polwart | B01L 3/502707 506/40 |
| 2006/0172408 A1 | 8/2006 | Quake et al. | |
| 2006/0233674 A1 | 10/2006 | Nelson | |
| 2006/0281183 A1 | 12/2006 | Sun et al. | |
| 2007/0029365 A1 * | 2/2007 | Paul | B32B 37/10 228/101 |
| 2007/0041878 A1 * | 2/2007 | Bryning | B01L 3/502738 422/504 |
| 2007/0134807 A1 | 6/2007 | Bao et al. | |
| 2007/0224617 A1 | 9/2007 | Quake et al. | |
| 2007/0248971 A1 | 10/2007 | Maerkl et al. | |
| 2008/0050283 A1 | 2/2008 | Chou et al. | |
| 2008/0075380 A1 | 3/2008 | Dube et al. | |
| 2008/0108063 A1 | 5/2008 | Lucero et al. | |
| 2008/0129736 A1 | 6/2008 | Sun et al. | |
| 2008/0176211 A1 | 7/2008 | Spence et al. | |
| 2008/0223721 A1 | 9/2008 | Cohen et al. | |
| 2008/0230387 A1 | 9/2008 | McBride et al. | |
| 2008/0241603 A1 * | 10/2008 | Isono | G11B 5/7315 428/846.9 |
| 2008/0264863 A1 | 10/2008 | Quake et al. | |
| 2008/0274493 A1 | 11/2008 | Quake et al. | |
| 2008/0281090 A1 | 11/2008 | Lee et al. | |
| 2008/0292504 A1 | 11/2008 | Goodsaid et al. | |
| 2009/0018195 A1 | 1/2009 | Balagadde | |
| 2009/0069194 A1 | 3/2009 | Ramakrishnan | |
| 2009/0142236 A1 | 6/2009 | Unger et al. | |
| 2009/0147918 A1 | 6/2009 | Fowler et al. | |
| 2009/0168066 A1 | 7/2009 | Hansen et al. | |
| 2009/0239308 A1 | 9/2009 | Dube et al. | |
| 2009/0291435 A1 | 11/2009 | Unger et al. | |
| 2010/0104477 A1 | 4/2010 | Liu et al. | |
| 2010/0120018 A1 | 5/2010 | Quake et al. | |
| 2010/0120077 A1 | 5/2010 | Daridon | |
| 2010/0154890 A1 | 6/2010 | Maerkl et al. | |
| 2010/0166608 A1 | 7/2010 | Quan et al. | |
| 2010/0171954 A1 | 7/2010 | Quake et al. | |
| 2010/0183481 A1 | 7/2010 | Facer et al. | |
| 2010/0184202 A1 | 7/2010 | McBride et al. | |
| 2010/0187105 A1 | 7/2010 | Unger et al. | |
| 2010/0196892 A1 | 8/2010 | Quake et al. | |
| 2010/0197522 A1 | 8/2010 | Liu et al. | |
| 2010/0200782 A1 | 8/2010 | Unger et al. | |
| 2010/0230613 A1 | 9/2010 | Pieprzyk et al. | |
| 2010/0263732 A1 | 10/2010 | Hansen et al. | |
| 2010/0263757 A1 | 10/2010 | Fernandes et al. | |
| 2010/0311060 A1 | 12/2010 | Facer et al. | |
| 2010/0320364 A1 | 12/2010 | Unger et al. | |

FOREIGN PATENT DOCUMENTS

| | | |
|---|---|---|
| JP | 2009-520371 A2 | 5/2009 |
| JP | 2010-165731 A2 | 7/2010 |
| WO | 01/01025 A2 | 1/2001 |
| WO | 01/67369 A2 | 9/2001 |
| WO | 2007/033385 A2 | 3/2007 |
| WO | 2007/044091 A2 | 4/2007 |
| WO | 2008/043046 A2 | 4/2008 |
| WO | 2009/100449 A1 | 8/2009 |
| WO | 2010/011852 A1 | 1/2010 |
| WO | WO 2010/011852 A1 | 1/2010 |
| WO | 2010/017210 A1 | 2/2010 |
| WO | 2010/077618 A1 | 7/2010 |
| WO | 2011/053790 A2 | 5/2011 |

OTHER PUBLICATIONS

Notification of Transmittal of the International Search Report and the Written Opinion of the International Searching Authority, or the Declaration and International Search Report and Written Opinion of the International Searching Authority for International Application No. PCT/US2009/051568 mailed on Oct. 29, 2009, 9 pages.

* cited by examiner

METHOD AND SYSTEM FOR MANUFACTURING INTEGRATED FLUIDIC CHIPS

CROSS-REFERENCES TO RELATED APPLICATIONS

The present application is a national phase entry under 35 U.S.C. §371 based on PCT Patent Application No. PCT/US2009/051568, filed Jul. 23, 2009, which claims benefit under 35 U.S.C. §119(e) of U.S. Provisional Patent Application No. 61/083,877, filed on Jul. 25, 2008, the disclosures of which are hereby incorporated by reference in their entirety for all purposes.

BACKGROUND OF THE INVENTION

The present invention relates generally to microfabricated structures and methods for producing microfabricated structures. Merely by way of example, embodiments of the invention provide methods of fabricating integrated fluidic chips useful for performing a variety of biological and chemical analyses. The scope of the methods and systems described herein is also applicable to the fabrication and operation of fluidic devices used in regulating the flow of fluids.

Various approaches have been utilized to fabricate microfluidic pumps and valves. One method of producing microelectromechanical (MEMS) structures that include pumps and valves is silicon-based bulk micro-machining. This is a subtractive fabrication method in which single crystal silicon is lithographically patterned and then etched to form three-dimensional structures. Another method of producing MEMS structures that include pumps and valves is surface micro-machining. This is an additive method in which layers of semiconductor-type materials such as polysilicon, silicon nitride, silicon dioxide, and various metals are sequentially added and patterned to make three-dimensional structures.

A limitation of the first approach of silicon-based micro-machining is that the stiffness of the semiconductor materials used in the process necessitates high actuation forces, which in turn result in large and complex designs. In fact, both bulk and surface micro-machining methods are limited by the stiffness of the materials used in the particular process. In addition, adhesion between various layers of the fabricated device presents problems for reliable operation. Another limitation of the first approach is that wafer bonding techniques are generally employed to create multilayer structures. A limitation of the second approach is that thermal stresses between the various layers of the device limits the total device thickness, often to approximately 20 µm. Using either of the above methods, clean room fabrication and careful quality control are typically required.

The present assignee has developed methods and systems for fabricating integrated (i.e., monolithic) fluidic chips including elastomeric structures based on a multilayer, soft lithography process. As described in U.S. Pat. No. 6,793,753, the disclosure of which is hereby incorporated by reference in its entirety for all purposes, multilayer elastomeric structures can be fabricated that include one or more layers that support fluid flow as well as one or more layers configured to control the flow of these fluids.

Despite the advances made in techniques related to the fabrication of such integrated fluidic chips, there is a need in the art for improved methods and systems for fabricating microfluidic devices.

SUMMARY OF THE INVENTION

The present invention provides methods related to the production of microfabricated structures. Merely by way of example, embodiments of the invention provide methods of fabricating integrated fluidic chips useful for performing a variety of biological and chemical analyses. The scope of the methods and systems described herein is also applicable to the fabrication and operation of fluidic devices used in regulating the flow of fluids.

According to an embodiment of the present invention, a method of manufacturing one or more integrated fluidic chips is provided. The method includes providing a first substrate having one or more mold features formed thereon and forming a first elastomeric layer on the first substrate. The first elastomeric layer is defined by a mold surface and a back surface. The method also includes joining the back surface of the first elastomeric layer to a support substrate. The method further includes providing a second substrate having one or more second mold features formed thereon and forming a second elastomeric layer on the glass substrate. The second elastomeric layer is defined by a mold surface and a back surface. Moreover, The method includes aligning the glass substrate to the support substrate and bonding the mold surface of the first elastomeric layer to the back surface of the second elastomeric layer.

According to another embodiment of the present invention, a method of manufacturing one or more integrated fluidic chips is provided. The method includes providing a substrate having a first surface area greater than 28 square inches, forming a plurality of mold features on the substrate, and forming a layer including an elastomeric material overlying the substrate and the plurality of mold features. The method also includes providing a second substrate have a second surface area greater than 28 square inches, forming a second plurality of mold features on the second substrate, and forming a second layer including a second elastomeric material overlying the second substrate and the second plurality of mold features. The method further includes bonding the layer to the second layer.

According to a particular embodiment of the present invention, an integrated fluidic chip is provided. The integrated fluidic chip includes a substrate defined by a lateral surface area greater than 28 square inches and a first elastomeric layer having a mold surface and a top surface. The mold surface of the first elastomeric layer is joined to a portion of the substrate. The first elastomeric layer includes a plurality of first channels extending normally from the substrate to a first dimension inside the first elastomeric layer. The integrated fluidic chip also includes a second elastomeric layer having a mold surface and a top surface. The mold surface of the second elastomeric layer is joined to at least a portion of the top surface of the first elastomeric layer.

According to another particular embodiment of the present invention, an integrated fluidic chip is provided. The integrated fluidic chip includes a substrate and an elastomeric structure joined to the substrate. The elastomeric layer includes a first layer having a plurality of flow channels having a width less than 1000 µm and a plurality of chambers in fluid communication with the plurality of flow channels. A combined volume of the plurality of chambers is greater than 115 µl. The elastomeric layer also includes a second layer having a plurality of control channels having a width less than 1000 µm. The second layer is disposed in a plane parallel to the first layer.

According to a specific embodiment of the present invention, an array of fluidic devices is provided. The array of fluidic devices includes a substrate defined by a lateral surface area greater than or equal to 18 square inches. The array of fluidic devices also includes a first set of fluidic devices arranged in a first geometry. Each of the first set of fluidic devices includes a plurality of first channels disposed in a plane parallel to the substrate and extending a predetermined distance from the substrate into a first elastomeric layer and a plurality of second channels disposed in a plane parallel to the substrate and extending a second predetermined distance from the first elastomeric layer into a second elastomeric layer. The array of fluidic devices further includes a second set of fluidic devices arranged in a second geometry. Each of the second set of fluidic devices includes a second plurality of first channels disposed in the plane parallel to the substrate and extending the predetermined distance from the substrate into the first elastomeric layer and a second plurality of second channels disposed in the plane parallel to the substrate and extending the second predetermined distance from the first elastomeric layer into the second elastomeric layer.

Numerous benefits are achieved using the present invention over conventional techniques. For example, an embodiment according to the present invention provides a method to manufacture integrated fluidic chips with increased throughput and reduced cost. Additionally, embodiments provide scalable chip designs that are applicable to technologies other than biological system analysis. Some of the manufacturing processes described herein leverage proven technology and incorporate novel fabrication steps to provide an increased number of devices per substrate, larger devices providing increased functionality, or combinations thereof. Moreover, some embodiments provide scalable manufacturing processes that are transferable to processing of substrate having larger sizes. Depending upon the embodiment, one or more of these benefits may exist. These and other benefits have been described throughout the present specification and more particularly below.

DETAILED DESCRIPTION OF SPECIFIC EMBODIMENTS

Figure 1A:
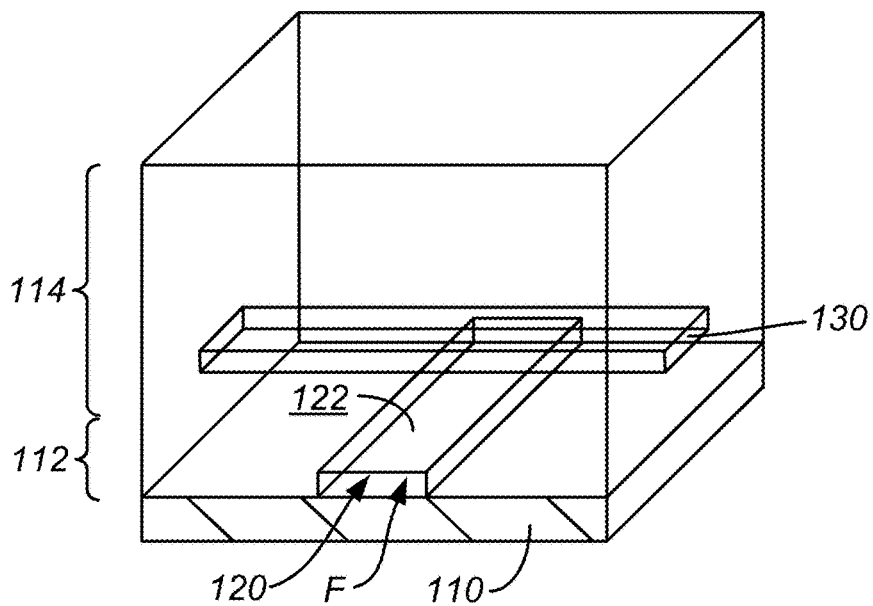
FIG. 1A is a simplified schematic diagram of a portion of an integrated fluidic chip according to an embodiment of the present invention.

FIG. 1A is a simplified schematic diagram of a portion of an integrated fluidic chip according to an embodiment of the present invention. As illustrated in FIG. 1A, a substantially planar substrate 110 (e.g., a glass substrate) supports two layers 112 and 114 that are formed as a monolithic structure. The first layer 112 includes a flow channel 120 with top surface 122. Fluid materials illustrated by F are able to flow through the flow channel 120 in a direction extending into and out of the plane of FIG. 1 based on pressure applied at other portions of the flow channel (not illustrated). A second layer 114 includes a control channel 130 extending at an angle (an angle of 90° in the embodiment illustrated in FIG. 1) with respect to the flow channel. A membrane is provided to separate the flow channel 120 from the control channel 130 at the location where the two channels intersect.

Figure 1B:
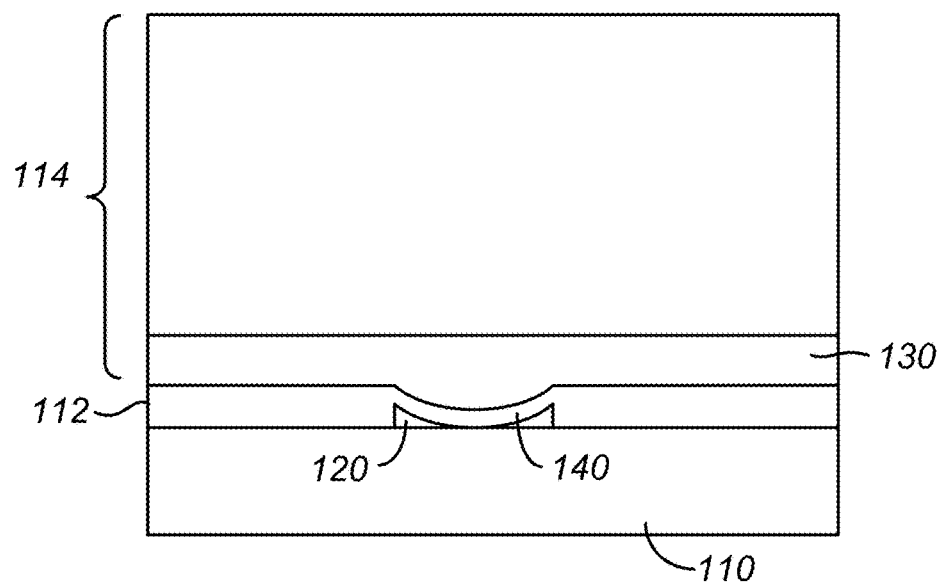
FIG. 1B is a simplified schematic diagram of a portion of an integrated fluidic chip in an actuated position according to an embodiment of the present invention.

FIG. 1B is a simplified schematic diagram of a portion of an integrated fluidic chip in an actuated position according to an embodiment of the present invention. As can be seen in FIG. 1B, pressurization of flow channel 130 (e.g., either by gas or liquid introduced therein) causes membrane 140 to deflect downward, thereby pinching off the flow of fluid passing through flow channel 120. Accordingly, by varying the pressure in control channel 130, a linearly actuable valving system is provided such that flow channel 120 can be opened or closed by moving membrane 140 as desired.

Although FIGS. 1A and 1B illustrate flow channel 120 positioned between the substrate 110 and the control layer 130, this particular geometry is not required by embodiments of the present invention. In other embodiments, the control channel is disposed below the flow channels (i.e., push up valves). Moreover, although only a single layer of flow and control are illustrated in FIGS. 1A and 1B, some embodiments utilize additional flow and or control layers as appropriate to the particular applications. Additionally, although a normally open valve is illustrated in FIGS. 1A and 1B, normally closed valves are also provided by embodiments described herein. One of ordinary skill in the art would recognize many variations, modifications, and alternatives.

In a specific embodiment, the substrate 110 is fabricated from a glass layer that is transparent, allowing optical interrogation of the elastomeric channels and reservoirs formed in the elastomeric material layers.

The inventor has determined that widespread adoption of integrated fluidic chip (IFC) products will most likely require that the integrated fluidic chips themselves be made inexpensively and in large numbers. Thus, embodiments of the present invention provide efficient manufacturing processes, workflows, and apparatus useful in manufacturing IFCs in large volumes. Currently, IFCs are fabricated using 6" diameter silicon substrates or wafers as transfer substrates. The silicon wafer itself has no part or function in the final IFC product, but merely provides a high precision substrate that is compatible with commercially available semiconductor processing equipment. Conventional process flows using such 6" silicon wafers are described in U.S. Pat. No. 6,793,753, previously referenced.

Figure 2A:
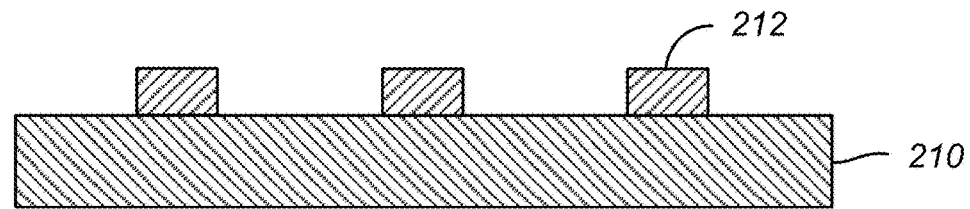
FIGS. 2A-2J illustrate a simplified process flow for fabricating an IFC according to an embodiment of the present invention.
Figure 2B:
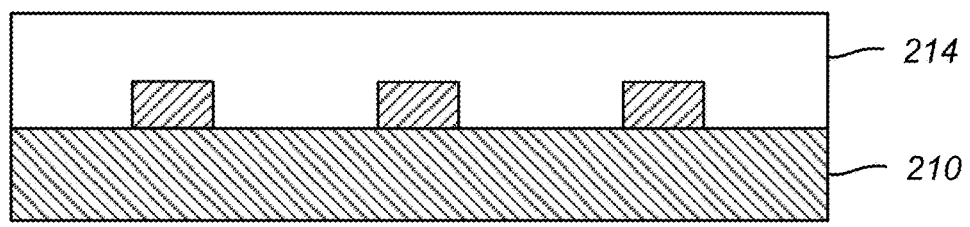

FIGS. 2A-2J illustrate a simplified process flow for fabricating an IFC according to an embodiment of the present invention. FIG. 2A illustrates a substrate 210 with a number of mold features 212 formed on an upper surface of the substrate. The substrate is typically an FPD plate, such as a Gen 2 panel. The mold features, which are typically formed from a photoresist layers that is coated and patterned on the substrate, have a feature size on the order of tens of microns. As will be described throughout the present specification, the mold features provide a space in which fluid channels are formed in subsequent processing steps. FIG. 2B illustrates the formation, typically through a knife coating process, of an elastomeric layer 214 overlying the substrate and the mold features. In the illustrated embodiment, the thickness of the elastomeric layer (e.g., PDMS) is on the order of the mold features, thereby forming a layer that encapsulates the mold features and provides a thin layer overlying the mold features suitable for formation of the membrane illustrated in FIG. 1B.

Figure 2C:
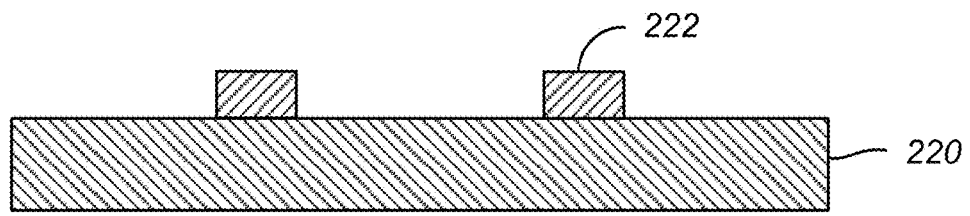

FIG. 2C illustrates a second substrate 220 with a number of mold features 222 formed thereon. An elastomeric layer 224 (e.g., PDMS) is formed overlying the substrate and the mold features. In general, the methods utilized to form the elements illustrated in FIGS. 2A and 2B are also applicable to FIGS. 2C and 2D. It should be noted that in some embodiments, the thickness of the second elastomeric layer 224 is much thicker than the height of the mold features. For example, the second elastomeric layer is typically 4 mm thick, although other thicknesses are included within the scope of the present invention.

Figure 2D:
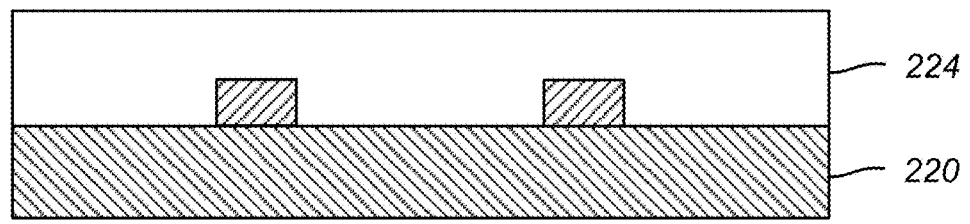
Figure 2E:
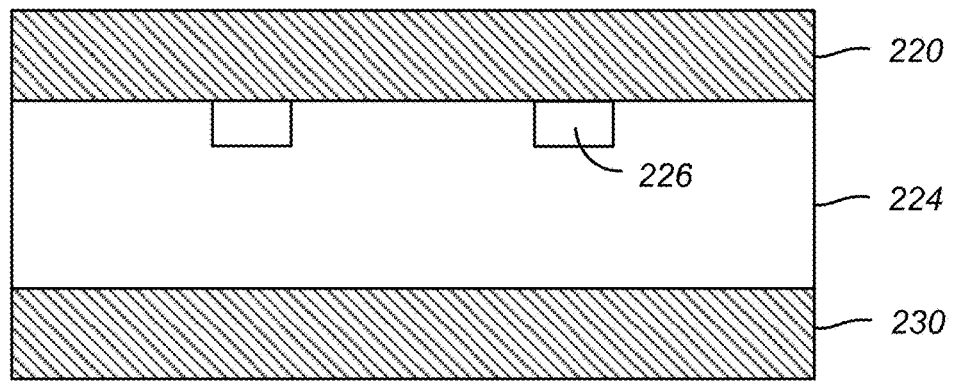
Figure 2F:
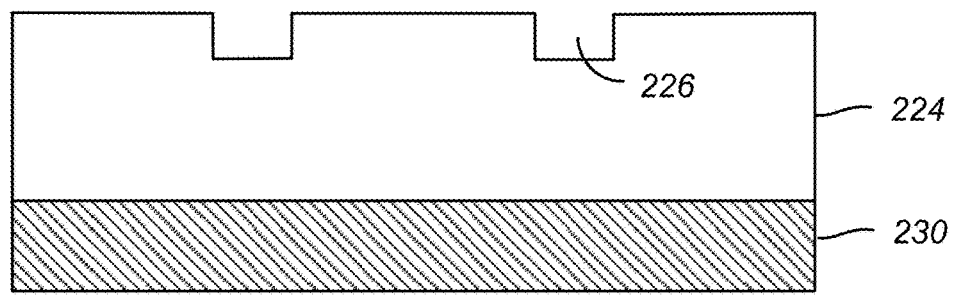

FIG. 2E illustrates the structure fabricated in FIG. 2D in an inverted configuration and bonded to a substrate 230. The substrate 230 is typically an FPD plate, such as a Gen 2 panel. Substrate 220 is removed as illustrated in FIG. 2F to expose the mold features 222, which are then removed to provide channels 226. These channels 226 will be used as fluid flow or control channels in some device designs. It should be noted that the elastomeric structure 224 remains bonded to substrate 230 during subsequent processing steps, which provides mechanical rigidity during fabrication.

Figure 2G:
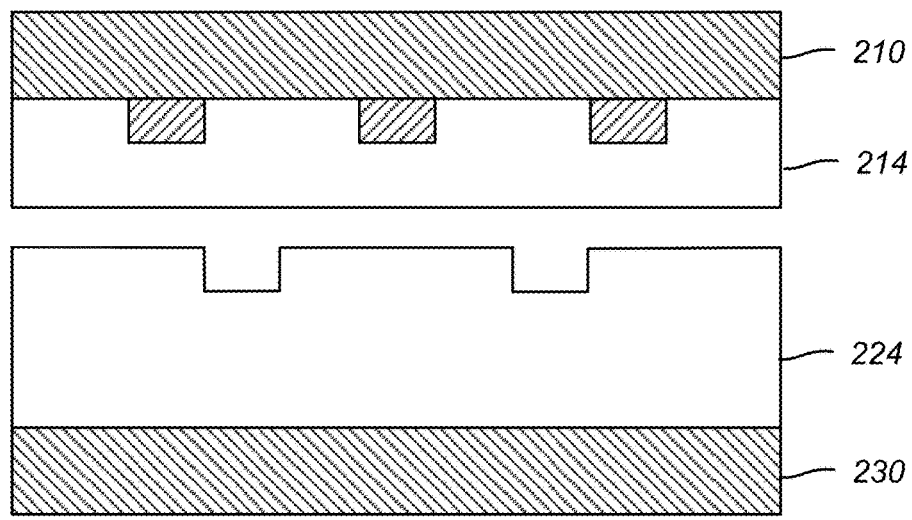
Figure 2H:
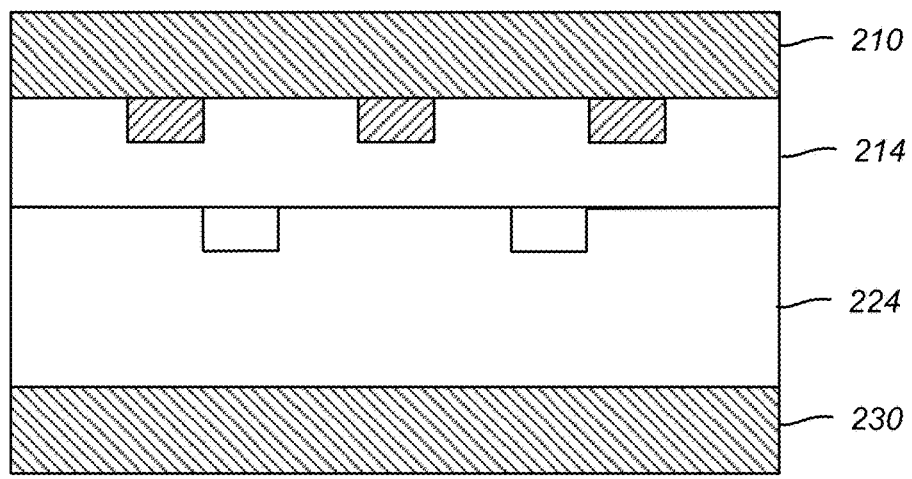

FIG. 2G illustrates the structure of FIG. 2B in an inverted configuration positioned above the structure of FIG. 2F. In this portion of the manufacturing process, the substrates are aligned so that the channels and devices formed in the two elastomeric material layers can be aligned to each other. As will be evident to one of skill in the art, the alignment provides for a desired overlap between the channels in the flow and control layers as described more fully throughout the present specification. FIG. 2H illustrates the bonding of the two structures previously illustrated during alignment in FIG. 2G. Plasma enhanced bonding processes are utilized in some embodiments to provide a permanent seal between the elastomeric layers. One of ordinary skill in the art would recognize many variations, modifications, and alternatives.

Figure 2I:
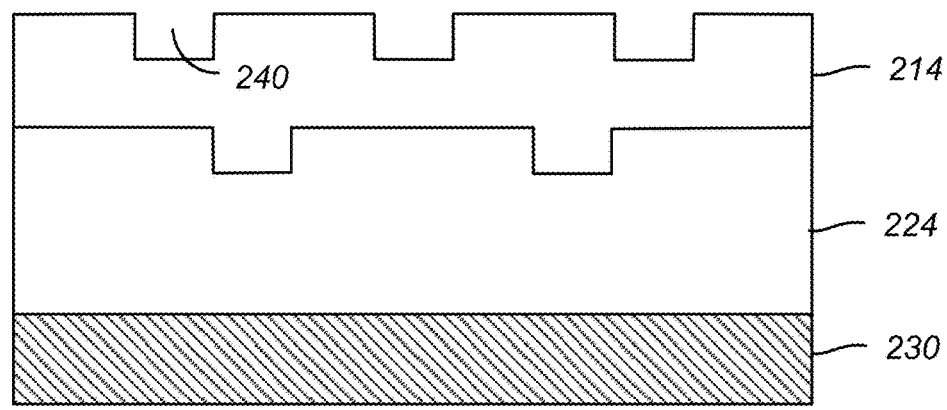
Figure 2J:
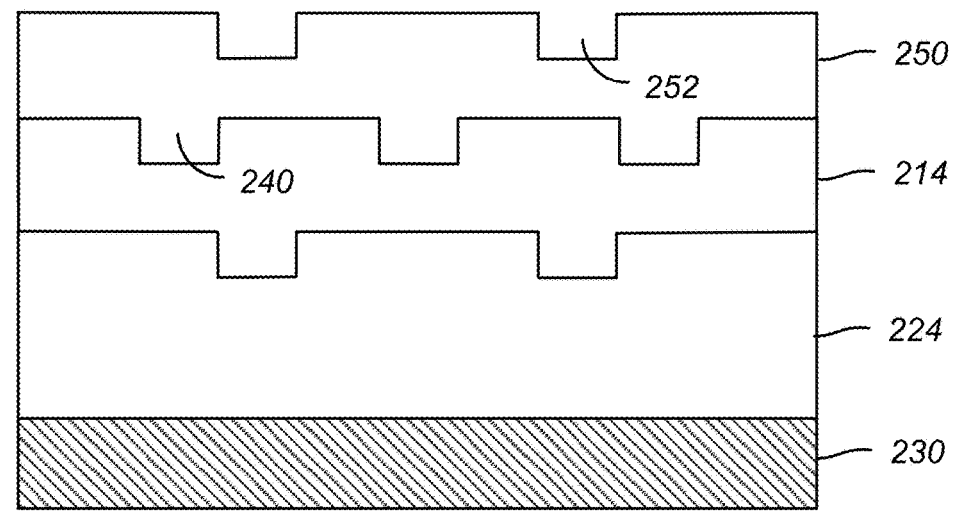

FIG. 2I illustrates the removal of substrate 210 from the bonded elastomeric structure illustrated in FIG. 2H. Removal of substrate 210 exposes the mold features 212, which are subsequently removed using plasma ashing in the case of photoresist mold features or other suitable processes to form channels 240. Thus, as illustrated in FIG. 2I, the channels 240 are free of material. Additional layers may be formed on other substrates including mold features and then bonded to the structure illustrated in FIG. 2I. As illustrated in FIG. 2J, an additional elastomeric layer 250 including a number of channels 252 has been fabricated and bonded, thereby providing three elastomeric material layers. The layer 250 can be fabricated using processes similar to those used for layer 214. Additional layers can be provided in other embodiments and the illustrations shown in FIGS. 2A-2I are merely provided by way of example and are not intended to limit the scope of the present invention. As discussed previously, the illustrated orientations of the various channels in the several elastomeric layers is not intended to limit embodiments of the present invention but only to represent the presence of channels, which may run in various directions through the elastomeric layers. Moreover, vias passing from channels in one layer to other channels in another layer are not illustrated for purposes of clarity. Furthermore, reaction chambers provided in fluid communication with the channels are not illustrated for purposes of clarity. One of ordinary skill in the art would recognize many variations, modifications, and alternatives.

Figure 3:
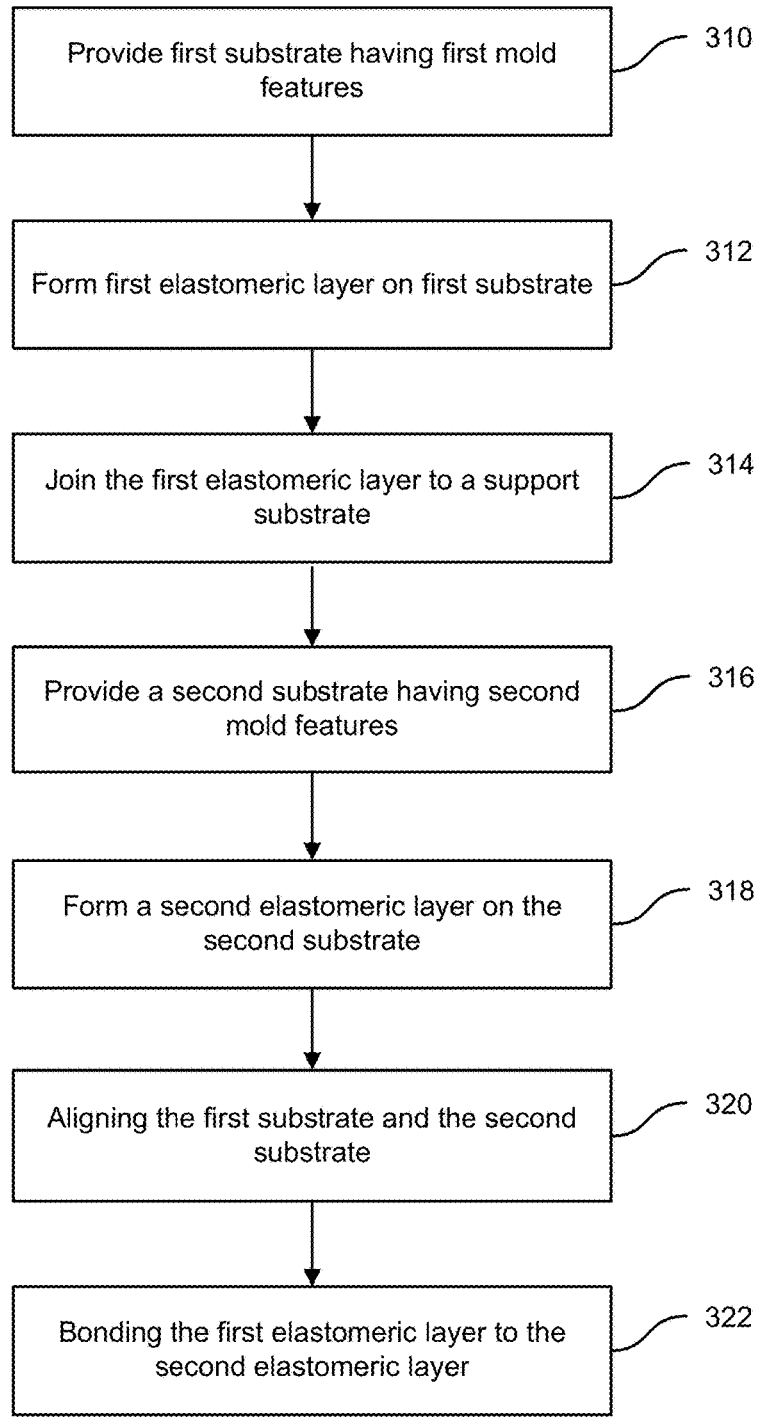
FIG. 3 is a simplified flowchart illustrating a method of fabricating an IFC according to an embodiment of the present invention.

FIG. 3 is a simplified flowchart illustrating a method of fabricating an IFC according to an embodiment of the present invention. As illustrated in FIG. 3, the method includes providing a first substrate having first mold features (310). Generally, the first substrate is an FPD panel and the mold features are formed using patterned photoresist. A first elastomeric layer is formed on the first substrate (312), encapsulating the mold features and making contact with portions of the first substrate. For some thicker layers, the elastomeric layer is formed using an enclosed molding process. The first elastomeric layer is joined to a support substrate (314). In some embodiments, the support substrate forms one portion of the enclosed mold used during formation of the first elastomeric layer. The first elastomeric layer is generally not separated from the support substrate during a number of subsequent processing steps until a device dicing process is performed. Thus, although joining the first elastomeric layer to the support substrate is illustrated in FIG. 3 as a process following the formation of the first elastomeric layer, this is not required by embodiments of the present invention since processes 312 and 314 can occur concurrently.

The method also includes providing a second substrate having second mold features (316) and forming a second elastomeric layer on the second substrate (318). As described more fully throughout the present specification, the second elastomeric layer is typically formed using a knife coating process rather than a spin coating process. The first and second substrates are aligned (320) and the first and second elastomeric layers are bonded together (322) to form a monolithic elastomeric structure.

It should be appreciated that the specific steps illustrated in FIG. 3 provide a particular method of fabricating an IFC according to an embodiment of the present invention. Other sequences of steps may also be performed according to alternative embodiments. For example, alternative embodiments of the present invention may perform the steps outlined above in a different order. Moreover, the individual steps illustrated in FIG. 3 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 4:
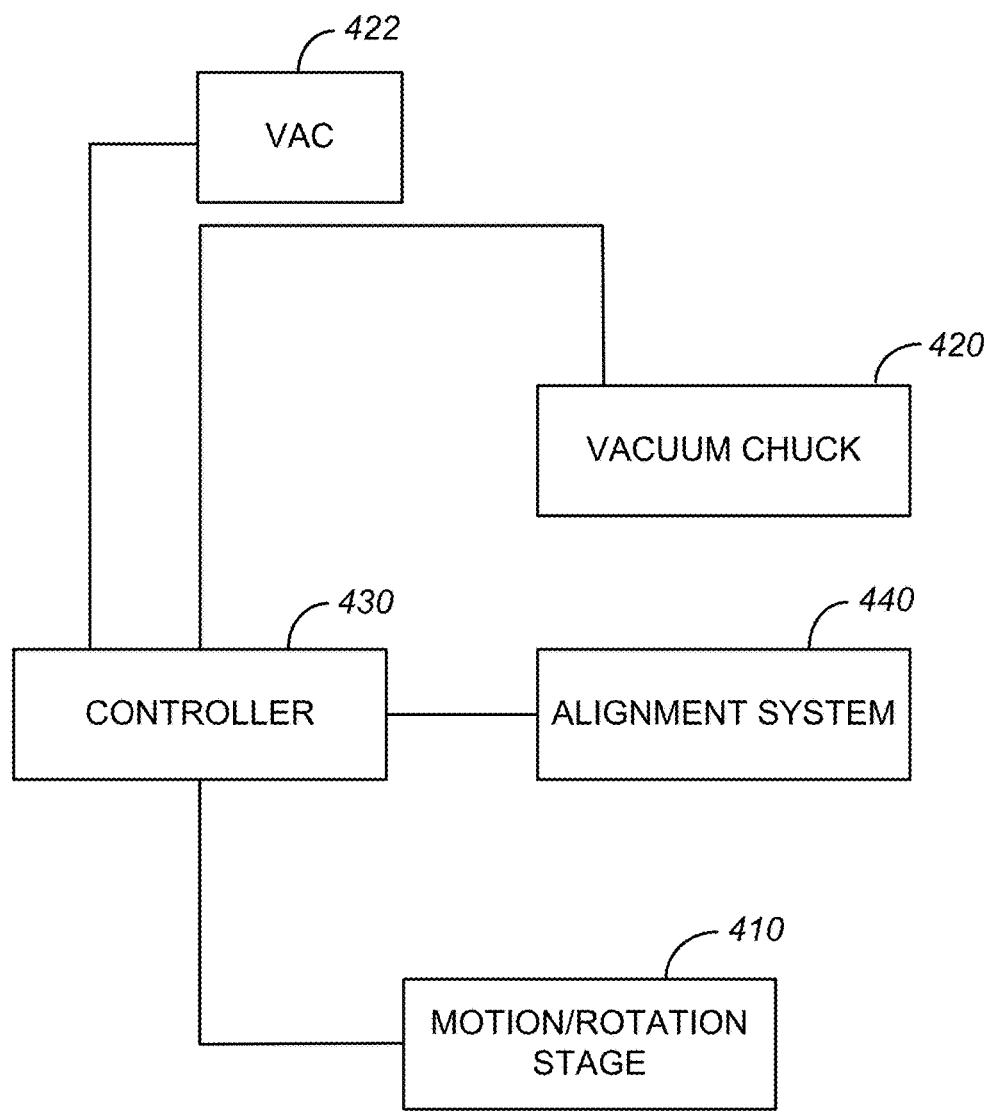
FIG. 4 is a simplified schematic diagram of an IFC fabrication system according to an embodiment of the present invention.

FIG. 4 is a simplified schematic diagram of an IFC fabrication system according to an embodiment of the present invention. A vacuum chuck 420 is provided in communication with controller 430. The controller 430, which is also in fluid communication with a vacuum source 422, is configured to provide controllable vacuum levels to the vacuum chuck. According to an embodiment, the vacuum chuck is configured to provide different vacuum levels as a function of position, for example, a higher vacuum level at peripheral portions than at central portions. A motion/rotation stage 410 is provided in communication with controller in the embodiment illustrated in FIG. 4 although this is not required by embodiments of the present invention. The motion/rotation stage provides four degrees of freedom in one embodiment, three motion directions and rotation. In other embodiments, tilt is provided by the stage so that five or six degrees of freedom are available.

Figure 5:
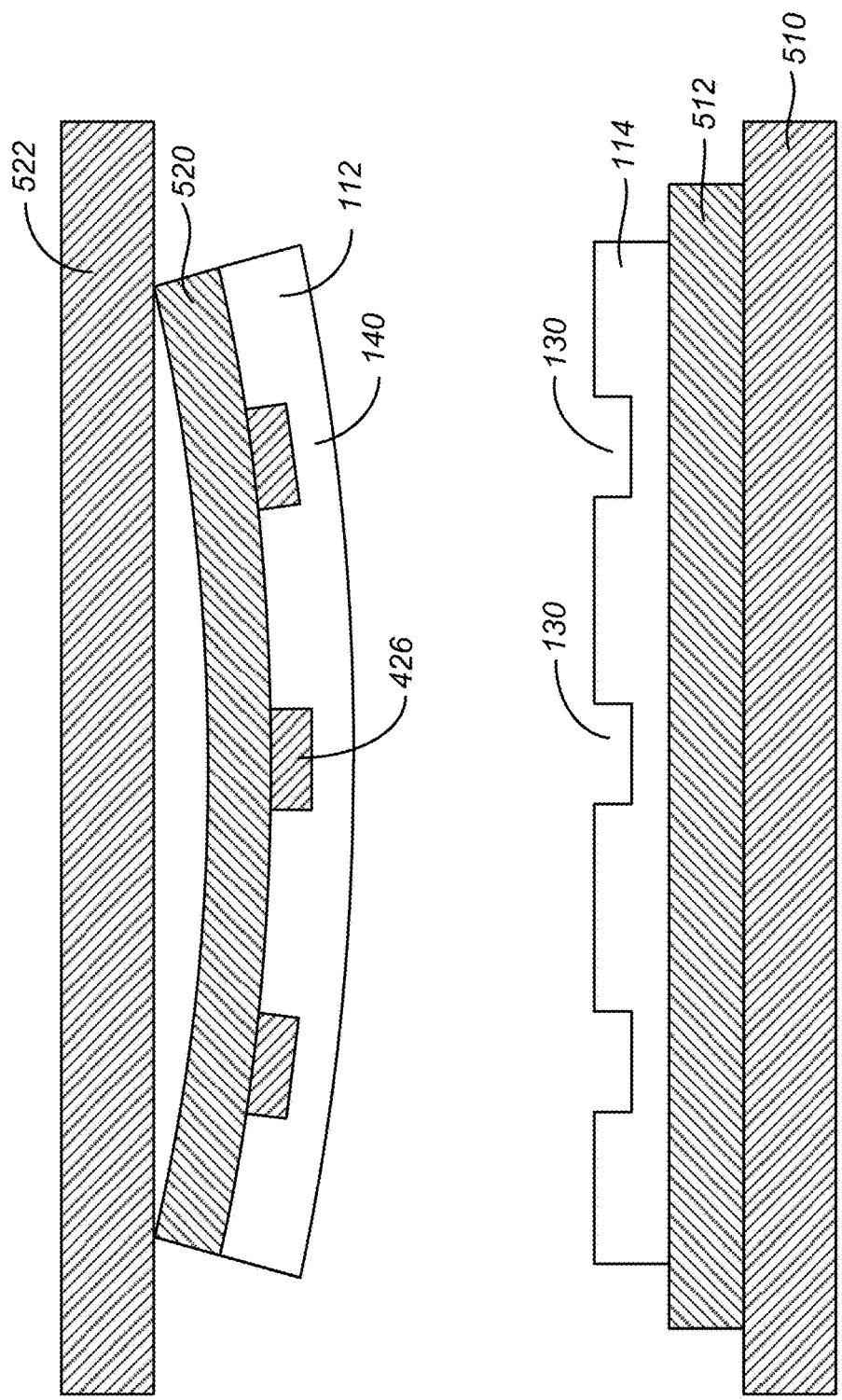
FIG. 5 is a simplified schematic diagram of a layer-to-layer alignment technique according to an embodiment of the present invention.

A first substrate is suspended in an inverted position by the vacuum chuck 420 and a second substrate is supported by the motion/rotation stage 410. Vacuum chucking (not illustrated) may be provided to the motion/rotation stage 410 in some embodiments. As an example, FIG. 5 illustrates two substrates positioned in a system as illustrated in FIG. 4. The variable vacuum as a function of position enables the substrate supported by the vacuum chuck 420 to sag in the center as described in more detail throughout the present specification.

An alignment system 440 is provided and is illustrated as being in communication with controller 430. It should be noted that similar to the motion/rotation stage 410, it is not necessary that the alignment system 440 be controlled by the controller since both of these elements can be independently controlled by another controller (not shown) or by a system operator. The alignment system 440 is used to align the substrates as illustrated in FIG. 2G prior to bonding of the elastomeric layers formed on the substrates. Accordingly, the alignment system may include one or more cameras, monitors, optical elements, and the like. One of ordinary skill in the art would recognize many variations, modifications, and alternatives. A particular system provided according to an embodiment of the present invention includes the elements illustrated in FIG. 4 as well as two panels having elastomeric materials formed thereon as illustrated in FIG. 5. The top panel, which is typically an FPD plate, is allowed to sag under its own weight, or with application of a predetermined amount of vacuum, in order to reduce or eliminate the presence of air bubbles in the monolithic elastomeric structure after bonding.

FIG. 5 is a simplified schematic diagram of a layer-to-layer alignment technique according to an embodiment of the present invention. As illustrated in FIG. 5, the first elastomeric layer 114 is supported on a thick glass substrate 512. For purposes of illustration, the first elastomeric layer (referred to herein as the control layer and illustrated as layer 214 in FIG. 2B) includes control channels 130. This exemplary illustration is not intended to limit the scope of the present invention but to only provide an example in order to illustrate a manufacturing process. The layer is formed and then cured in some embodiments. Typically, the raised features (referred to as mold features) are formed using photoresist or other suitable material that is patterned on the silicon wafer leaving a raised line of photoresist where a channel is desired. The first elastomeric layer is deposited over the raised features to a depth greater than the height of the raised features. After subsequent fabrication steps, described below, the photoresist is removed by dissolving it out of the elastomeric with an appropriate solvent, with the voids formed by removal of the photoresist becoming the flow channels passing through the flow layer.

In a specific embodiment, the glass substrate 512 is an FPD plate such as a Gen 2 plate measuring 370 mm×470 mm. In other embodiments, other glass plates including other generation FPD plates are utilized. As will be evident to one of skill in the art, the first elastomeric layer is generally formed and then cured prior to bonding. The first elastomeric layer is supported over the entire surface area of the slab or layer, not just at the peripheral edges. As illustrated in FIG. 5, it remains in contact with the glass plate that forms the ceiling of its enclosed mold (e.g., an FPD panel, a ⅜" thick glass sheet, solid plastic sheet, a sacrificial film applied to a glass or plastic sheet, or the like) throughout the entire manufacturing process until the IFCs are ready for dicing.

A second elastomeric layer (illustrated as the layer including the flow channels for purposes of clarity) is supported in an inverted configuration by a thin glass substrate 520 (e.g., an FPD plate) that is supported, in turn, by vacuum contact with a vacuum chuck 522. The second elastomeric layer (referred to herein as the flow layer for purposes of illustration) is layer 112 in FIG. 1 that includes the flow channels and the membrane 140 between the flow channels and the control channels. In FIG. 5, the control channels are illustrated as extending from the plane of the figure, but this particular illustration is merely for ease of illustration in showing the vertical position of the control channels in the elastomeric layer and it will be understood that the control channels may extend in other directions as appropriate to the particular application. The FPD glass panel is suspended by vacuum, allowing the center portion of both the glass substrate 520 and the second elastomeric layer 112 to sag by a predetermined amount.

In one embodiment, the substrate 520 is held at its perimeter by vacuum and the center is allowed to sag under its own weight with the amount of sag controlled by another vacuum controller. The inventor has determined that when the first and second elastomeric layers are joined together in a subsequent processing step, the illustrated sag provides for a bonding front that begins at the center portion of the first elastomeric layer and emanates in a substantially circular pattern toward the edges of the second elastomeric layer. Thus, air bubbles, which will typically form if two planar surfaces are joined, are pushed in a lateral direction toward the edges of the layers, thereby preventing formation of air pockets (i.e., entrapment of air bubbles) in the finished device.

The inherent flexibility of FPD glass panels, which are typically 0.7 mm thick, provides for a predetermined sag in the elastomeric layer that is suitable for methods described herein. In other embodiments, the amount of vacuum pressure applied to the center and peripheral portions of the FPD plate 520 is adjusted to provide a predetermined sag.

The two pieces or layers of patterned elastomeric material (typically PDMS) are brought together with high geometric precision as described below. The inventor has determined that the high geometric precision provided by the methods described herein is one of the developments that have made the fabrication of multi-layer chips possible. Referring to FIG. 5, the substrate 512 supporting the first elastomeric layer 114 is positioned in a fixture 510. The fixture is provided with controls that allow for micro-positioning in at least four axes (x, y, z, θ). In other embodiments, additional degrees of freedom (e.g., tilt) are provided by the fixture. Fewer or additional degrees of freedom are provided in alternative embodiments.

Embodiments of the present invention provide for improved alignment of the various channels in the two layers. As illustrated in FIG. 5, the use of glass plates with the same (or similar) CTEs to support the elastomeric layers reduces misalignment resulting from expansion differences during thermal processing. Additionally, with respect to the second elastomeric layer, since the FPD glass panel 520 flexes under its own weight to produce the desired sag in some embodiments, the sagging results in reduced stretching of the elastomeric layer, thereby improving alignment tolerances.

Table 1 illustrates the CTEs for silicon, PDMS and glass materials. The effect of a 1° C. temperature change on the substrate and on layer to layer alignment are also illustrated in Table 1. Since some embodiments do not remove the IFC material (e.g., PDMS) from the substrate during fabrication, no distortion of the IFC material results during processing. Additionally, since the layers of the IFC are all fabricated on glass substrates, any mismatch in CTE is minimized, thereby reducing the constraints placed on temperature control during processing.

TABLE 1

| Fabrication Process | Material | Coefficient of Thermal Expansion (CTE) | 1° C. Effect on Substrate | 1° C. Alignment Error |
|---|---|---|---|---|
| 6" Wafer | Silicon wafer | $2.6 \times 10^{-6}$ C.$^{-1}$ | 0.4 µm | 40.3 µm |
|  | PDMS | $270 \times 10^{-6}$ C.$^{-1}$ | 41 µm |  |
| Gen 2 FPD Plate (370 mm × 470 mm) | ECM glass | $4.6 \times 10^{-6}$ C.$^{-1}$ | 2.2 µm | 0.7 µm |
|  | LCD glass | $4.5 \times 10^{-6}$ C.$^{-1}$ | 2.1 µm |  |
|  | Photomask glass | $3.25 \times 10^{-6}$ C.$^{-1}$ | 1.5 µm |  |

It will be noted that the use of FPD plates during the manufacturing of IFCs provides a number of benefits in comparison to conventional fabrication techniques. For example, the large size of FPD plates in comparison to silicon wafers enables the fabrication of an increased number of IFC devices of a given size during a fabrication run, thereby increasing throughput and reducing production costs. Additionally, the rectangular geometry of the FPD plates corresponds more closely to the generally rectangular geometry of IFCs, thereby decreasing the unused area of the substrate in comparison to circular silicon substrates. Thereby, additional improvements in throughput and reductions in cost are provided.

In order to join the first elastomeric and the second elastomeric layers together, the layers are optically aligned and brought together such that the center portions of the layers touch first, thus reducing the likelihood of trapping air bubbles as described above. Support of the first elastomeric layer, which may be several millimeters thick (e.g., 4 mm thick), reduces or eliminates stretching of this layer, which may result in misalignment between the layers after bonding. Such misalignment can adversely affect the relative positions of the various channels in the two layers.

Figure 7:
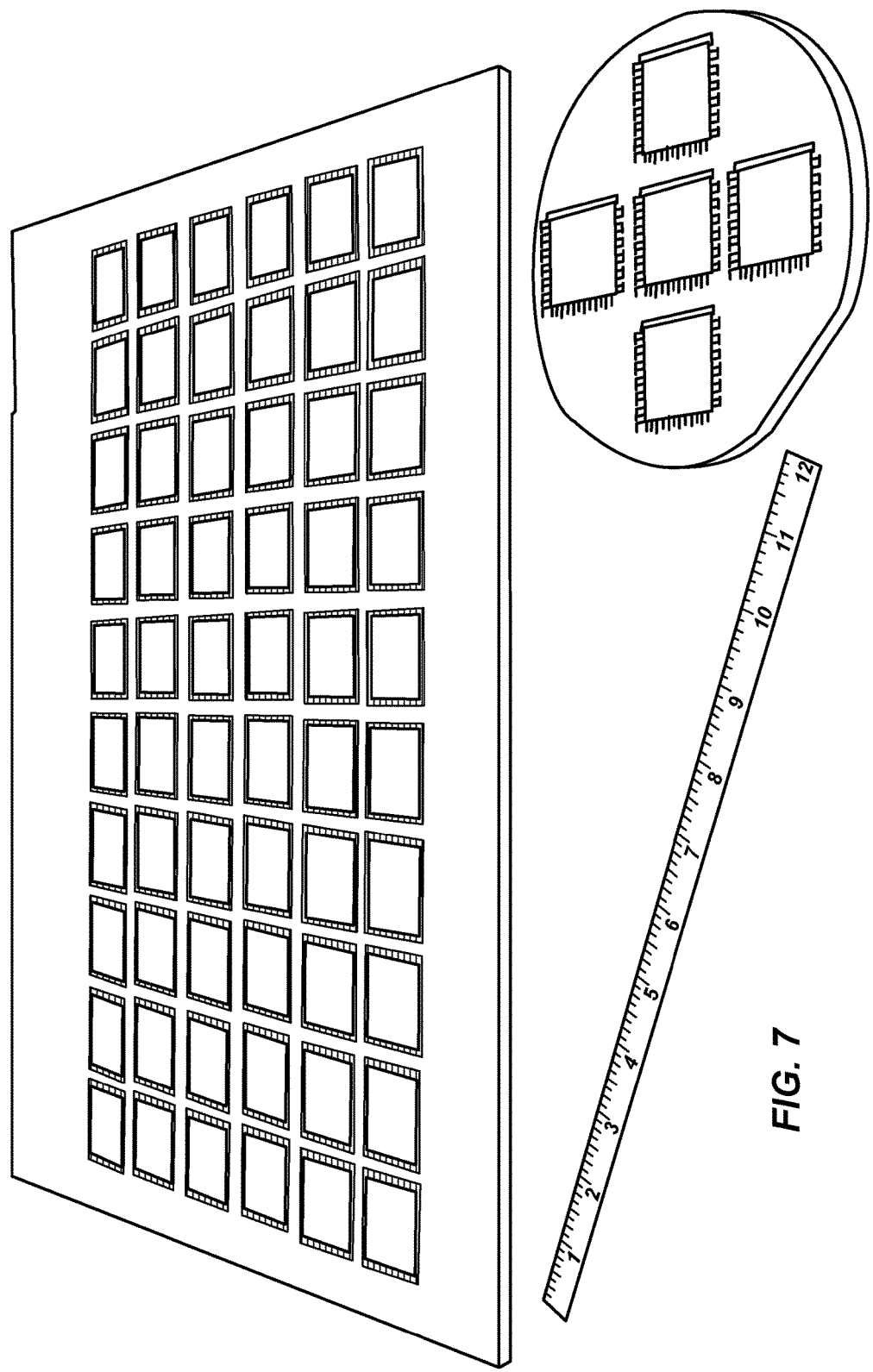
FIG. 7 is a photograph illustrating an array of IFCs fabricated on an FPD panel and an array of IFCs fabricated on a 6" silicon wafer according to embodiments of the present invention.

FIG. 7 is a photograph illustrating an array of IFCs fabricated on an FPD panel and an array of IFCs fabricated on a 6" silicon wafer according to embodiments of the present invention. As shown in FIG. 7, the number of IFCs is increased by the use of a larger substrate. Additionally, the form factor of the rectangular FPD panel provides for an increase in the ratio of active device space to total substrate area, thereby reducing the amount of PDMS material wasted during fabrication. One of ordinary skill in the art would recognize many variations, modifications, and alternatives.

In order to facilitate the alignment process, fiducials and verniers are provided in some embodiments at predetermined locations on the FPD plate. For example, alignment fiducials may be provided at one or more peripheral portions of the plate to assist in initial alighnment between plates. Interlocking fiducials or other appropriate alignment marks are imaged and aligned by moving one or both of the FPD plates under operator or computer control. In order to provide fine alignment, verniers are also provided at predetermined locations at peripheral or central portions of the plate. In an example, verniers or other suitable fine alignment marks are provided at peripheral portions of the substrates. Table 2 illustrates alignment tolerances that have been achieved for several panels. As illustrated in Table 2, without the use of temperature or vibration control, alignment accuracy of ±30 µm has been achieved. The inventor believes that additional calibration of the optical system will further improve the alignment accuracy.

TABLE 2

| Panel # | Absolute Average Deviation (µm) | | Average Deviation (µm) | | Largest Deviation (µm) | Number of Measurements |
|---|---|---|---|---|---|---|
|  | X | Y | X | Y |  |  |
| 1 | 41 | 21 | 41 | 20.6 | 60 | 10 |
| 2 | 35.5 | 24.5 | −33.1 | 7.1 | 70 | 9 |
| 3 | 17.4 | 12.6 | 13.9 | −1.0 | 70 | 11 |
| 4 | 23.7 | 6.8 | 22.2 | 5.1 | 40 | 11 |

In addition to providing methods and systems for supporting, aligning, and bonding elastomeric layers, embodiments of the present invention provide methods and systems for forming elastomeric (e.g., PDMS) layers on large area glass substrate including FPD plates. Some methods of fabrication provided by embodiments of the present invention utilize spin coating techniques to for the elastomeric layers. In one of these spin coating methods, liquid PDMS is deposited in a puddle in the center of a wafer and then the wafer is spun. Centrifugal forces serve to spread the PDMS evenly on the wafer with the resulting layer thickness being a function of spin speed, spin time, and initial volume deposited. Excess PDMS flows over the edges of the wafer and is typically discarded. Although such spin methods may be scalable to Gen2 size FPD panels, it is likely that the amount of PDMS utilized for such large panels would be high since much of the liquid PDMS would be wasted after flowing over the edge of the wafer. Additionally, since FPD panels are rectangular, the quality of spin coated layers formed on FPD plates may not be as high as similar layers formed on circular substrates.

In an embodiment of the present invention, an extrusion die coating process is utilized in place of a spin coating process. In another embodiment, a drawbar coating process is utilized in place of a spin coating process. Either of these two methods are useful to form or otherwise deposit a thin layer of PDMS or other elastomeric onto a FPD panel. In extrusion die coating a slot die that is the same width as the FPD panel passes over the FPD panel at a predetermined distance (e.g., 50 µm) from the top surface of the panel. The mold features formed on the FPD panel are encapsulated in the elastomeric material extruded from the slot die. As the slot die moves over the panel, the elastomeric (e.g., PDMS) is pumped through the slot die at a predetermined rate, which is typically precisely metered, resulting in a uniform coating of PDMS over both the panel and the mold features previously formed on the panel. In an embodiment, the PDMS is allowed to self-level at room temperature on a flat surface and then baked to cure. According to embodiments of the present invention, a layer of elastomeric (e.g., PDMS) is formed that is characterized by a thickness ranging from about 5 µm to about 500 µm, for example, from about 10 µm to about 150 µm.

In an alternative embodiment, a drawbar coater having one of a variety of shapes (e.g., straightedge, comma, Meyer, or the like) is utilized to form a uniform elastomeric layer similar to those formed using an extrusion die. In drawbar coating processes, the PDMS or other elastomeric material is dispensed onto the panel in front of the coating head, not by the coating head. Because both extrusion die and drawbar coating machines have been used in FPD manufacturing processes, currently available equipment can be modified for use in formation of PDMS layers as described herein.

As discussed above, utilizing FPD plates rather than silicon substrates for support of PDMS layers during fabrication processes provides a greater number of IFCs per substrate. For some applications, the IFC dimensions are on the order of 2 cm×5 cm. In other applications, the IFC dimensions are larger, for example, on the order of 43 cm×43 cm, 8 cm×12 cm, 9 cm×13 cm, 37 cm×47 cm, or the like. Some IFC dimensions are in between the sizes listed above. The particular example of an IFC with dimensions on the order of 8 cm×12 cm (e.g., 87 mm×127 mm) corresponds to the size of some micro-titer plates, enabling the IFC to be a drop-in replacement in some micro-titer plate systems. However, embodiments of the present invention are not limited to providing a greater number of devices per substrate. In a particular embodiment, the size of an individual IFC is only limited by the size of the FPD plate, enabling the fabrication of IFCs with dimensions not possible using silicon wafers as fabrication substrates.

In addition to the benefits described above, the present invention provides a platform that enables the fabrication of a universal carrier IFC. The large IFC size provides an opportunity to integrate routing layers into the IFC, eliminate accumulators that are typically provided externally to the IFC, and enable more complex chip control. A universal carrier provides an interface (e.g., one or more routing layers) that enables a universal carrier to be used with a variety of different die sizes.

In some embodiments, multiple coating techniques are utilized depending on the thickness and material properties of the layers to be fabricated. For example, thin coatings (e.g., 10 µm to 50 µm in thickness) are formed using knife coating techniques and thicker coatings (e.g., 4 mm thick layers) are formed using spin coating techniques or enclosed molding techniques. In a particular embodiment utilizing knife coating techniques, multiple passes of the apparatus over the substrate are made to form a layer of elastomeric material during multiple passes.

Figure 6:
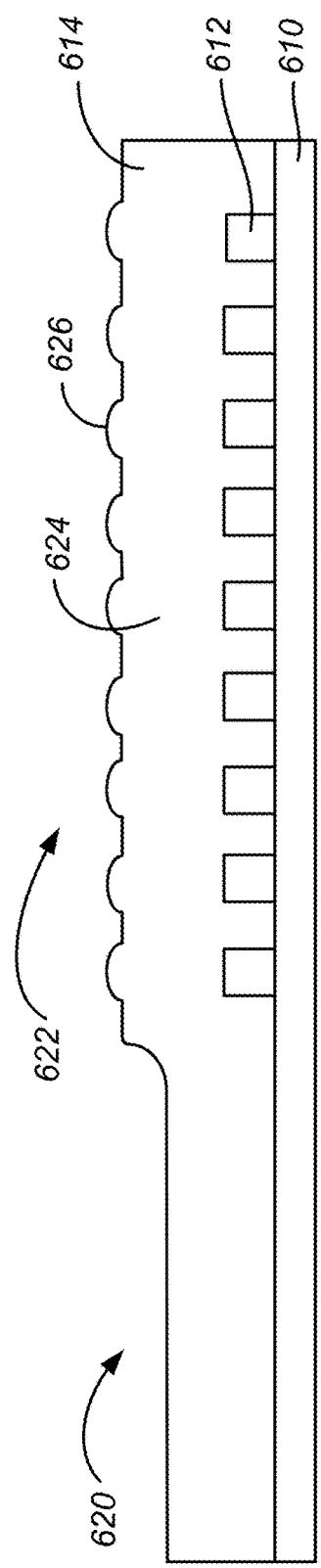
FIG. 6 is a simplified schematic diagram of an IFC fabrication system according to an embodiment of the present invention.

Utilizing embodiments of the present invention, the uniformity of extruded or drawn coatings is improved in comparison with spin coating techniques. The inventor has performed studies of coating uniformity that demonstrate that the techniques described above provide benefits not available using spin coating techniques. FIG. 6 illustrates a substrate after a PDMS formation process according to an embodiment of the present invention. The substrate 610 has mold features 612 formed thereon. A layer of PDMS 614 is formed over the substrate and the mold features, thereby filling the spaces between the mold features. As shown in FIG. 6, the presence of the mold features in an array pattern, which is typically of IFC structures, results in a variation of PDMS thickness during the PDMS formation process. Several areas are illustrated in FIG. 6: a blanket coating area off of the array features (620), a blanket coating area within the array features (622), a membrane area above the array of mold features (624), and microbumps (626) formed above the mold features (612).

Table 3 shows data collected for the various areas illustrated in FIG. 6 for a spin coating process as well as an extrusion process. In the studies illustrated by FIG. 6, a Gen 2 FPD plate was used as the substrate 610. The mold features were formed using photoresist and were characterized by a height of 15 µm. The spin coating measurements were made using a height profiler available from Veeco Instruments, Inc. of Plainview, N.Y. and the extrusion coating measurements were made by viewing a cross section under microscopy.

TABLE 3

| | Blanket Difference (µm) | Membrane Variance (µm) | Microbump Height (µm) |
| --- | --- | --- | --- |
| Spin Coating | 6.75 | 0.7 | 0.6 |
| Extrusion Coating | 0.72 | 1.4 | 0.4 |

The data in Table 3 illustrates that for a spin coating process on a Gen 2 FPD plate, the blanket difference, which is the thickness of the blanket area within the array minus the thickness of the blanket area off of the array, was markedly higher than that achieved using extrusion coating processes. Without limiting embodiments of the present invention, the inventor believes that the practical elimination of this blanket difference using extrusion results from the decoupling of the layer thickness from the material viscosity provided by use of knife coating techniques in comparison with spin coating techniques. In spin coating processes, the thickness of the layer is a function of the spin speed and the material viscosity. As the spin speed increases, the thickness decreases. In contrast, the knife coating methods described herein provide a layer thickness that can be designed to achieve a predetermined thickness with a reduced impact as a result of material viscosity. Thus, embodiments of the present invention provide methods of forming layers characterized by thicknesses only achievable at high spin speeds for PDMS and similar elastomeric materials. The variation in the membrane thickness and the height of the microbumps are similar independent of the PDMS formation method. Thus, despite the large size of the substrate, embodiments provide methods for elastomeric material formation that are compatible with IFC design rules.

In an alternative embodiment of the present invention, fluoroacrylate or parylene are utilized as mold coatings with decreased release forces in comparison to conventions 1 materials. Additionally a dry film photoresist may utilized to replace or supplement the knife coating process.

The alignment accuracy provided by embodiments of the present invention opens up opportunities to decrease features sizes in the IFC, which were previously constrained by layer to layer alignment tolerances. Additionally, the reductions in deposition thickness variation described herein provide for reductions in the design rules for the layers and the membrane thickness. As an example, the reduction in microbump height and the practical elimination of the blanket difference as illustrated in Table 3 enables IFC designs with reduced PDMS layer thicknesses. Thus, feature density and device functionality are increased by using the fabrication methods and systems described throughout the present specification.

The fabrication methods described herein are not limited to biological sample analysis applications. For example, in an embodiment, a fuel cell is fabricated using one or more elastomeric layers formed according to the methods described herein. The fuel cell includes a plurality of elastomeric layers through which fluids are able to move during operation of the fuel cell. The large substrate size provided by embodiments of the present invention enables the fabrication of large area fuel cell structures including microfluidic channels, valves, chambers, and the like. Thus, microfluidic functionality is provided in a device operating at macrofluidic levels.

In another embodiment, one or more components of a water purification system are fabricated using the techniques described herein. Similar to the fuel cell application, the IFCs fabricated using the methods and systems described herein are applicable to water purification systems since they provide microfluidic functionality on macrofluidic scales. Thus, embodiments of the present invention provide IFCs with a large number of microscale components or a massively parallel system built on microscale components. Thus, although the various device features are small, the large substrate surface area enables the fabrication of IFCs with large fluid volumes. Additionally, it should be noted that embodiments of the present invention are also applicable in the area of process intensification applications, which benefit from microfluidics configured to support a large total amount of fluid.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of manufacturing one or more integrated fluidic chips, the method comprising:
   providing a first substrate having one or more mold features formed thereon;
   forming a first elastomeric layer on the first substrate, wherein the first elastomeric layer is defined by a mold surface and a back surface;
   joining the back surface of the first elastomeric layer to a support substrate;
   providing a glass substrate having one or more second mold features formed thereon;
   forming a second elastomeric layer on the glass substrate, wherein the second elastomeric layer is defined by a mold surface and a back surface;
   aligning the glass substrate to the support substrate, wherein a central portion of the glass substrate sags toward the support substrate; and
   after the aligning, bonding the mold surface of the first elastomeric layer to the back surface of the second elastomeric layer.

2. The method of claim 1 wherein joining the back surface of the first elastomeric layer is performed concurrently with forming the first elastomeric layer.

3. The method of claim 1 wherein the glass substrate is characterized by a surface area greater than 50 square inches.

4. The method of claim 1 wherein the glass substrate is characterized by a waviness of 60 nm over an 8 mm window.

5. The method of claim 1 wherein the glass substrate is characterized by a waviness of 330 nm over an 25 mm window.

6. The method of claim 1 wherein the glass substrate is characterized by a thickness of less than 1 mm.

7. The method of claim 1 wherein the glass substrate is free from inclusions greater than 100 µm in size.

8. The method of claim 1 wherein the glass substrate comprises a rectangular plate characterized by a dimension greater than or equal to 370 mm×470 mm.

9. The method of claim 1 wherein the support substrate comprises a glass member.

10. The method of claim 9 wherein a coefficient of thermal expansion of the support substrate and a coefficient of thermal expansion of the glass substrate are within 300% of each other.

11. The method of claim 1 further comprising removing the first substrate from contact with the mold layer of the first elastomeric layer prior to bonding the mold surface of the first elastomeric layer to the back surface of the second elastomeric layer.

12. The method of claim 1 wherein aligning the glass substrate to the support substrate comprises positioning the glass substrate above the support substrate.

13. The method of claim 1 wherein the central portion sags by a displacement of greater than 50 µm and less than 1 cm from a line connecting opposing edges of the glass substrate.

14. The method of claim 1 wherein the one or more integrated fluidic chips comprise a plurality of integrated fluidic chips.

15. The method of claim 14 wherein the plurality of integrated fluidic chips comprises six or more integrated fluidic chips.

16. The method of claim 1 wherein bonding the mold surface of the first elastomeric layer to the back surface of the second elastomeric layer comprises a plasma-enhanced bonding process.

17. The method of claim 1 wherein forming the first elastomeric layer comprises at least one of an extrusion process or a drawbar coating process.

18. The method of claim 17 wherein the first elastomeric layer is characterized by a first thickness over a portion of the one or more mold features and a second thickness over a portion of the first substrate free from the one or more mold features, a difference between the first thickness and the second thickness is less than 2 µm.

19. The method of claim 17 wherein the first elastomeric layer is characterized by a first thickness over a portion of the one or more mold features and a second thickness over a portion of the first substrate free from the one or more mold features, a difference between the first thickness and the second thickness being less than 20%.

20. The method of claim 1 wherein forming the second elastomeric layer comprises an extrusion process.

21. The method of claim 1 wherein forming the first elastomeric layer comprises at least one of an extrusion process or a drawbar coating process.

22. A method of manufacturing one or more integrated fluidic chips, the method comprising:
   providing a substrate having a first surface area greater than 28 square inches;
   forming a plurality of mold features on the substrate;
   forming a layer including an elastomeric material overlying the substrate and the plurality of mold features;
   providing a glass substrate have a second surface area greater than 28 square inches;
   forming a second plurality of mold features on the glass substrate;
   forming a second layer including a second elastomeric material overlying the glass substrate and the second plurality of mold features; and
   bonding the layer to the second layer, wherein, prior to or during the bonding, a central portion of the glass substrate sags toward the substrate having the first surface area greater than 28 square inches.

23. The method of claim 22 wherein the first surface area is greater than 50 square inches and the second surface area is greater than 50 square inches.

24. The method of claim 22 wherein the first layer includes one or more integrated fluidic device structures defining an active area, a ratio of the active area to the first surface area is greater than 60%.

25. The method of claim 22 wherein the elastomeric material comprises PDMS.

26. The method of claim 22 wherein the second elastomeric material comprises PDMS.

27. The method of claim 22 wherein:
the layer comprises a mold surface and a back surface;
the second layer comprises a mold surface and a back surface; and
bonding the layer to the second layer comprises joining the mold surface of the layer to the back surface of the second layer.

28. The method of claim 27 further comprising joining the back surface of the layer to a support substrate.

29. The method of claim 28 further comprising aligning the glass substrate to the support substrate wherein a central portion of the glass substrate to sag toward the support substrate.

30. The method of claim 29 wherein the central portion is characterized by a sag of greater than 50 μm and less than 1 cm from a line connecting opposing edges of the glass substrate.

31. The method of claim 28 further comprising removing the substrate from contact with the layer prior to joining the mold surface of the layer to the back surface of the second layer.

32. The method of claim 22 wherein the substrate comprises a first glass member.

33. The method of claim 32 wherein the glass substrate is characterized by a thickness of less than 1 mm.

34. The method of claim 32 wherein the glass substrate is free from inclusions greater than 100 μm in size.

35. The method of claim 22 wherein a coefficient of thermal expansion of the substrate and a coefficient of thermal expansion of the glass substrate are within 300% of each other.

36. The method of claim 22 wherein bonding the layer to the second layer comprises a plasma-enhanced bonding process.

37. The method of claim 22 wherein forming the layer and forming the second layer comprise at least one of an extrusion process or a drawbar coating process.

38. The method of claim 37 wherein the layer is characterized by a first thickness over a portion of the plurality of mold features and a second thickness over a portion of the substrate free from the plurality of mold features, a difference between the first thickness and the second thickness being less than 2 μm.

39. The method of claim 37 wherein the second layer is characterized by a first thickness over a portion of the second plurality of mold features and a second thickness over a portion of the second substrate free from the second plurality of mold features, a difference between the first thickness and the second thickness being less than 2 μm.

* * * * *